United States Patent [19]
Eisum

[11] Patent Number: 5,789,249
[45] Date of Patent: Aug. 4, 1998

[54] METHOD FOR CALIBRATING AN ANALYSIS SYSTEM, AND AN ANALYSIS SYSTEM

[75] Inventor: Niels Eisum, Risskov, Denmark

[73] Assignee: Danfoss A/S, Nordborg, Denmark

[21] Appl. No.: 750,918

[22] PCT Filed: Jun. 27, 1995

[86] PCT No.: PCT/DK95/00268

§ 371 Date: Jan. 8, 1997

§ 102(e) Date: Jan. 8, 1997

[87] PCT Pub. No.: WO96/01989

PCT Pub. Date: Jan. 25, 1996

[30] Foreign Application Priority Data

Jul. 12, 1994 [DE] Germany ............... 44 24 494.0

[51] Int. Cl.$^6$ ............................................. G01N 31/00
[52] U.S. Cl. ............... 436/8; 436/52; 436/177; 436/178; 422/68.1; 422/81; 73/1.02
[58] Field of Search ............................. 436/8, 52, 177, 436/178; 422/62, 68.1, 81; 73/1.02; 204/401

[56] References Cited

U.S. PATENT DOCUMENTS 4,587,219  5/1986  Claren et al. .................. 422/103 X
4,973,561  11/1990  Hansen et al. ...................... 436/52
5,124,042  6/1992  Bredeweg et al. ................ 436/178 X
5,238,853  8/1993  Calzi et al. ......................... 436/68
5,293,770  3/1994  Hansen et al. .................... 436/8 X
5,672,319  9/1997  Eisum .............................. 422/82.02

FOREIGN PATENT DOCUMENTS 2725757  12/1978  Germany.
1427257  9/1988  U.S.S.R.

*Primary Examiner*—Maureen M. Wallenhorst
*Attorney, Agent, or Firm*—Lee, Mann, Smith, McWilliams, Sweeney & Ohlson

[57] ABSTRACT

A method is disclosed for calibrating an analysis system having a membrane, the outside of which is in contact with a medium to be analyzed, in order to detect a concentration of a species there, and a corresponding analysis system. In this connection it is desirable to be able to perform a calibration in situ. In this calibration, a first fluid of a predetermined first concentration of the species is conveyed along the inside of the membrane, at least a second fluid of a predetermined second concentration which differs from the first concentration is likewise conveyed past the inside of the membrane and the concentrations of the two fluids after passing the inside of the membrane are recorded. From these concentrations, parameters for a correlation between the concentration on the outside of the membrane and a measurement signal are ascertained.

12 Claims, 1 Drawing Sheet

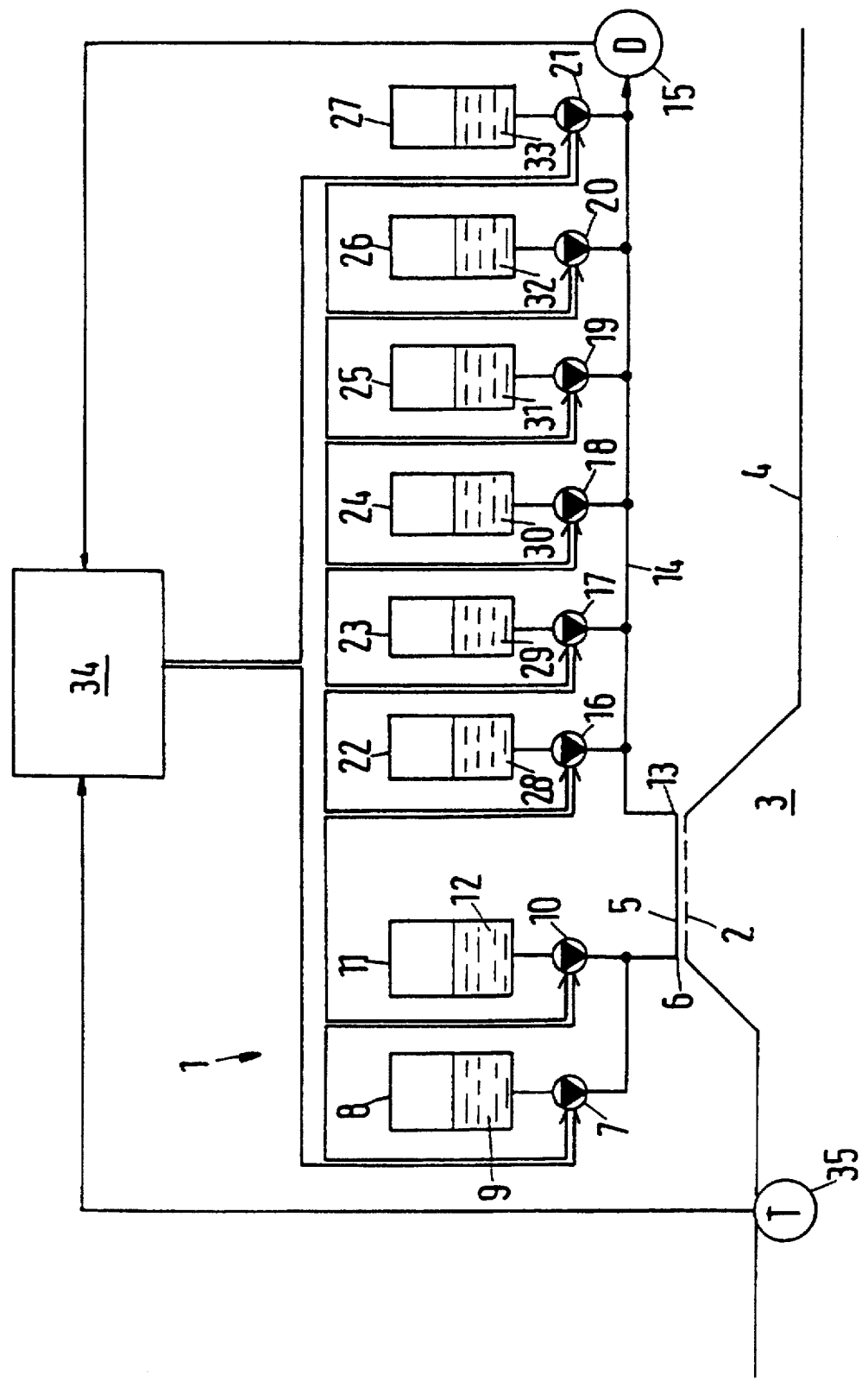

METHOD FOR CALIBRATING AN ANALYSIS SYSTEM, AND AN ANALYSIS SYSTEM

BACKGROUND OF THE INVENTION

The invention relates to a method for calibrating an analysis system having a membrane, the outside of which is in contact with a medium to be analyzed, in order to detect a concentration of a species there, and to an analysis system having a membrane, the outside of which is in contact with a medium to be analyzed, a flow path being arranged on the inside of the membrane, which flow path is connected on its input side to a reservoir for a carrier liquid and on its output side to a detector.

In analysis systems of that kind, the species to be detected, for example, ions or other particles, for example, low-molecular particles, pass from the fluid to be analyzed, which is present at or flows past the outside of the membrane, into a carrier fluid which flows past the inside of the membrane. Mostly, the fluids are liquids. The following description is therefore made with reference to liquids.

It is known that such analysis systems have to be calibrated from time to time. Such a calibration is necessary at least whenever a new membrane is used. The membranes normally have only a limited service life. Although in principle they are of identical construction, variations do occur from membrane to membrane, which can be taken into account by means of a calibration.

For example, U.S. Pat. No. 5,293,770 discloses a calibration device in which a calibration liquid is contained in a vessel. To effect calibration, a sensor provided with the membrane is immersed in this vessel.

U.S. Pat. No. 4,587,219 discloses a different analysis system, in which a liquid to be examined is conveyed past the outside of the membrane. Alternatively, a calibration liquid can be used in place of the liquid to be investigated.

Such calibrations are easy to perform in a laboratory because the corresponding measurements can be effected in a controlled environment. Problems arise, however, when the analysis apparatus is not readily accessible, for example, when it is being used in a sewage treatment plant and is floating in the settling basin or in the main outfall. Corresponding difficulties also occur when the analysis apparatus is being used to test the water quality of a flowing body of water or a lake or the sea. In all these cases the analysis apparatus would have to be recovered, the calibration performed and the analysis apparatus then re-located again. The effort involved in this is in many cases too great. An aggravating factor is that it is precisely in the said application purposes that a repeated calibration is required, and in fact also during the service life of membrane, because the properties of the membrane may change, for example, because of algal or other live growths or because of mechanical stresses, such as waves, for example, or because of ageing phenomena which are accelerated by changing temperatures.

SUMMARY OF THE INVENTION

The invention is based on the problem of allowing a calibration to take place in situ, that is, on site. This problem is solved in a method of the kind mentioned in the introduction in that a first fluid of a predetermined first concentration of the species is conveyed along the inside of the membrane, that at least a second fluid of a predetermined second concentration which differs from the first concentration is conveyed past the inside of the membrane, that the concentrations of the fluids after passing the inside of the membrane are recorded and from these concentrations parameters for a correlation between the concentration of the species on the outside of the membrane and a measurement signal are ascertained.

During the actual measuring process, a carrier liquid is conveyed past the membrane. From the concentration of the species in the carrier liquid, which is created as the carrier liquid flows past the membrane, one can now deduce the concentration of the species in the liquid to be analyzed. The following law applies:

$$\ln [1-(C^*-C)/(C_d-C)] = -k_o * A/Q_a \qquad (1)$$

in which $C$ is the concentration in the carrier liquid before it flows past the membrane, $C^*$ is the concentration in the carrier liquid after is has flowed past the membrane, $C_d$ is the (unknown) concentration in the liquid to be analyzed, $k_o$ is a mass transfer coefficient, $A$ is the effective area of the membrane and $Q_a$ is the flow volume per time along the membrane.

(see "Synthetic Membranes: Science, Engineering and Applications", Bungay, P. M., Lonsdale, H. K., de Pinho, M. N., D. Reidel Publishing Company., Dordrecht/Boston/Lancaster/Tokyo, page 629).

There are three unknowns, namely, the unknown concentration $C_d$ to be determined, and the two variables of the membrane, namely, the mass transfer coefficient $k_o$ and the effective area $A$. The last two factors are combined to form a product, so that they can be regarded as one unknown. The initial concentrations of the two liquids which are conveyed along the membrane are known. The final concentrations after they have passed the membrane can be measured. There remain therefore two equations with two unknowns ($C_d$ and $k_o \times A$), from which both the unknown concentration in the liquid to be analyzed and the "transfer behaviour" of the membrane can be ascertained for the instant of calibration. The transfer behaviour is assumed to be constant for the subsequent measurements. Generally speaking, it need merely be assumed that the membrane is equally permeable to the species to be measured in both directions, that is, from the outside to the inside and from the inside to the outside. In that case, it is immaterial whether the first and the second concentration is greater or less than the concentration in the liquid to be analyzed. In many cases, however, the range in which the concentration in the liquid to be analyzed moves will be known. If the first and the second concentrations of the liquid used for the calibration are selected to be lower than the lowest expected value of the concentration in the liquid to be analyzed, this restriction need not be applicable. In the novel method it is therefore no longer necessary to remove the analysis apparatus from its measuring site or to ensure in some other way that the calibration liquid is conducted along the outside of the membrane, as was previously the case. On the contrary, the analysis apparatus can now be left at its measuring site. The calibration is effected by the corresponding liquids being conveyed along the inside of the membrane.

In a preferred construction, provision is made for the two fluids to be conveyed along the membrane at the same flow rate and/or in the same throughput volume. The expression $Q_a$ is therefore the same in both equations, which further simplifies solving of the set of equations.

It is also preferred for the concentration of one fluid to be zero. In this way a fluid of the value zero can be used for the initial concentration C of a fluid in the equation, which further simplifies solving of the equation system. The concentration of the species in the fluid to be analyzed is then given by:

$$C_x = (C_2 * C_1^*)/(C_2 - C_2^* + C_1^*) \quad (2)$$

Here, the indices 1 and 2 denote the first and second fluid respectively. In the first fluid, the initial concentration of the fluid is zero. Simplification of the equation simplifies implementation of the method, because considerably fewer adders, subtracters and multipliers have to be used and fewer computations are necessary in a program-controlled sequence.

Water is preferably used as the fluid of concentration zero. Water of the required purity is in many cases readily available. It is chemically neutral, and therefore requires no additional security or protective measures.

It is also preferred for a carrier liquid used in measuring to be one of the fluids. This carrier liquid must in any case be present in the analysis apparatus. It can therefore be used virtually without additional expense for the calibration as well, which further simplifies the calibration.

In a preferred construction, the fluids are conveyed past the membrane in immediately successive intervals. The risk that there will be changes with time in the membrane is therefore kept to a low level. One can therefore assume without worry that the right-hand side in the relation (1) will remain constant.

In a further preferred construction, provision is made for the fluids to be conveyed in a first step simultaneously and parallel to one another on different flow paths past the membrane, and in a second step for the fluids to be conveyed simultaneously and parallel to one another with the flow paths interchanged past the membrane. In this construction, a calibration can be carried out with the required accuracy even when the properties of the membrane change during the calibration. Although there are limits within which the changes can occur, the acceptable changes in the properties of the membrane during the calibration are nevertheless increased.

Before the fluids are conveyed past the membrane, a detector arranged behind the membrane in the direction of flow is preferably calibrated. The calibration of the detector is known per se. By calibrating the detector in advance the advantageous effect is achieved that the subsequent method steps serve exclusively for determining the parameters of the membrane. The calibration result is markedly improved by this means.

It is also preferred for the calibration to be repeated at predetermined intervals and/or in dependence on predetermined external conditions. Thus, for example, the calibration can be effected in an hourly cycle. Other time intervals are also possible of course. These will depend on the expected change in the properties of the membrane. On the other hand, the calibration can also be made to depend on external conditions, for example, temperature changes, the swell of the sea, that is, a mechanical stress, or sudden changes in the measuring signal. The result of successive measurements can be evaluated with greater reliability.

It is also preferred for the temperature of the membrane to be measured during calibration. Temperature has a certain influence on the permeability of the membrane. The permeability can then be taken into account during the calibration. The temperature of the membrane can be determined relatively easily. It coincides with sufficient approximation to the temperature of the liquid with which the membrane is in contact.

In an analysis system of the kind mentioned in the introduction, the problem is solved in that the input side of the flow path is connected to an auxiliary reservoir which is filled with a calibration liquid which in respect of a species to be analyzed has a different concentration from the carrier liquid, wherein flow control means which convey calibration liquid or carrier liquid past the membrane are provided between the reservoir and the auxiliary reservoir on the one hand and between the reservoir and the flow path on the other hand.

On the input side of the flow path there is normally provided only a reservoir for the carrier liquid. This serves to receive the ions, atoms or molecules diffusing or migrating through the membrane. By the simple expedient of providing here an additional reservoir containing a different liquid, an opportunity is created to calibrate the analysis apparatus on the spot.

It is preferred herein for the flow control means for each liquid to comprise a pump, the output of which is controllable. In this manner an accurate flow control is achieved, so that the following evaluation of the concentrations with regard to the calibration is dramatically simplified.

BRIEF DESCRIPTION OF THE DRAWING

The invention is described hereinafter with reference to a preferred embodiment in conjunction with the drawing, in which the single FIGURE shows a diagrammatic representation of an analysis apparatus.

DETAILED DESCRIPTION OF THE INVENTION

An analysis apparatus 1 has a membrane 2, the outside of which is in contact with a liquid 3 to be analyzed. The membrane 2 covers a window in a diagrammatically indicated housing 4.

On the inside of the membrane 2, that is, the side which faces towards the inside of the housing 4, there is provided a flow path 5, represented diagrammatically here by a line. The flow path 5 has an inlet 6 which is connected by way of a pump 7 to a reservoir 8 which contains a carrier liquid 9. The carrier liquid 9 can be, for example, water. The cross-section of the flow path 5 is known.

The input 6 of the flow path 5 is furthermore connected by way of a pump 10 to an auxiliary reservoir 11, which contains a calibration liquid 12. The only requirement made of the calibration liquid 12 is that it has a different concentration from the carrier liquid 9 in respect of a species to be measured in the liquid 3 by means of the analysis apparatus 1. This concentration can be higher or lower than the concentration of the corresponding species in the liquid 3 to be analyzed. It can also be the same as that concentration. Generally, however, the concentration of that species in the liquid 3 to be analyzed is unknown.

The flow path 5 has an outlet 13 which is connected by way of a reaction channel 14 to a detector 15. The reaction channel 14 is connected by way of pumps 16–21 to reservoirs 22–27, each of which contains a different liquid 28–33, for example, water or reagents. The reservoir 22 in particular, which is connected to the reaction channel 14 in the vicinity of the outlet 13 of the flow path 5, contains water.

The pumps 7, 10, 16–21 and the detector 15 are connected to a control unit 34. The control unit 34 can control each pump 7, 10, 16–21 individually. The pumps 7, 10, 16–21 each have a pump output that can be metered relatively accurately. With appropriate control by the control unit 34, the quantity $Q_a$ of the amounts of liquids delivered by the pumps 7, 10, 16–21 34 is also available to the control unit 34. Information is thus available about the amount of liquid that has been conveyed through the flow path. Gaseous fluids could also be used instead of liquids, of course.

For measurement, using the pump 7 the carrier liquid 9 is conveyed through the flow path 5 along the membrane 2. The species to be detected passes by diffusion or other transfer processes through the membrane 2 into the carrier liquid 9. The initial concentration C of the carrier liquid 9 is known. In the case of water, for example, it has the value zero.

In the reaction channel 14 reagents are added to the carrier liquid which is now of different concentration; the reagents lead, for example, to a precipitation or colour change reaction, which can be evaluated in the detector 15, which can be in the form of a photodetector, for example. The control unit 34 can convert the output signal of the detector 15 into a concentration value $C^*$. The following law applies here:

$$ln\ [1-*(C^*-C)/(C_d-C)]=-k_o * A/Q_a \tag{1}$$

in which

C is the concentration in the carrier liquid before it flows past the membrane, $C^*$ is the concentration in the carrier liquid after is has flowed past the membrane, $C_d$ is the (unknown) concentration in the liquid to be analyzed, $k_o$ is a mass transfer coefficient, A is the effective area of the membrane and $Q_a$ is the flow volume per time along the membrane.

From this, the control unit 34 is able to determine the concentration $C_d$ of the species in the liquid 3 to be analyzed.

Here, however, it is a prerequisite that the properties of the membrane, which appear primarily in the product $k_o \times A$, are known. These "transfer properties" of the membrane on the one hand change from membrane to membrane so that a calibration is required at least after every membrane change. But these properties may also change during the service life of the membrane as a result of environmental influences, for example, algal growth or the like. It is therefore in many cases also necessary to perform a calibration from time to time.

To carry out the calibration, first of all the reaction channel 14 is cleaned using the water 28 from the reservoir 22. By this means the detector 15 can be set to zero at the same time. If desired, the detector 15 can also be supplied with a liquid from one of the other reservoirs 23–27, which produces in the detector a measuring signal which can be used as such for calibration of the detector 15.

Once the detector 15 has been calibrated, carrier liquid 9 is passed in the usual manner using the pump 7 though the flow path 5 along the membrane 2. The initial concentration of the carrier liquid 9 in the reservoir 8 is known. As the carrier liquid 9 flows through the flow path 5 it becomes enriched with the species whose concentration in the liquid 3 to be analyzed is to be determined. Precipitation or colour change reactions that can be evaluated by means of the detector 15 are then produced in the reaction channel using the customary reagents. A signal is therefore obtained which provides information about the concentration of the species in the carrier liquid 9 after passing through the flow path 5.

In a second step, the calibration liquid 12 is now conveyed from the auxiliary reservoir 11 by means of the pump 10 through the flow path 5. The control unit 34 here ensures that the flow rate through the flow path 5 is the same as the flow rate of the carrier liquid 9 through the flow path. The factor $Q_a$ from the above relation therefore remains constant. The calibration liquid 12 has a different concentration of the species from the carrier liquid 9. As it flows through the flow path 5 it is either enriched with the species or it releases the species to the liquid 3 to be analyzed. In the rare cases in which the concentration of the species in the calibration liquid 12 and the liquid 3 to be analyzed is identical, no change in concentration will occur as the liquids pass through the flow path 5. In all cases, the concentration of the calibration liquid 12 in the reaction channel 14 can be detected using the same precipitation or colour change reactions that are caused here, just as they are in a normal measurement, by addition of reagents from the individual reservoirs 23–27. Also, the concentration in the calibration liquid after it has flowed past the membrane 2 is detected in the detector 15 and relayed to the control unit 34.

The calibration is effected in two intervals following immediately in succession. One can assume here that the transfer properties of the membrane have not changed. With the different concentrations, two equations are therefore held, the right-hand sides of which are identical. By equating, the following expression can be obtained:

$$(C_1^*-C_1)/(C_d-C_1)=(C_2^*-C_2)/(C_d-C_2) \tag{3}$$

Here, the indices 1, 2 denote the carrier liquid 9 (1) and the calibration liquid 12 (2) respectively. The order in which the calibration liquid and the carrier liquid are sent through the flow path is, of course, irrelevant.

From this relation (3), the concentration $C_d$ in the liquid 3 to be analyzed can now be detected. The following equation applies:

$$C_d=C_1+[(C_2-C_1) * C_1^*-C_1)]/[(C_2-C_2^*)+(C_1^*-C_1)] \tag{4}$$

This expression is simplified quite considerably if one of the two liquids is water, because this has an initial concentration $C_1=0$, the expression becoming:

$$C_d=(C_2 * C_1^*)/(C_2-C_2^*+C_1^*) \tag{2}$$

Once the concentration $C_d$ of the species in the liquid 3 to be analyzed is known, the parameter $k_o \times A$ can be calculated and stored for subsequent measurements.

A calibration of this kind can be carried out on the spot because it is sufficient to convey the corresponding liquids past the inside of the membrane 2. The analysis apparatus 1 need not therefore be removed from its measuring site. The calibration can be effected regularly at specific intervals and/or in dependence on external conditions, so that the measurement result can be obtained over a relatively long time with great reliability.

In addition, a temperature sensor 35 which detects the temperature of the liquid 3 to be analyzed and relays the temperature value to the control unit 34 can be provided. The temperature of the liquid 3 to be analyzed is virtually the same as the temperature of the membrane 2. The transfer behaviour or permeability of the membrane 2 is also determined by the temperature. The control unit 34 can therefore also take changing temperature influences into account in the subsequent measurement.

I claim:

1. A method for calibrating an analysis system having a membrane, an outside of which is in contact with a medium to be analyzed, in order to detect a concentration of a species therein, comprising the steps of conveying a first fluid of a predetermined first concentration of the species along an inside of the membrane, conveying at least a second fluid of a predetermined second concentration of the species which differs from the first concentration of the species past the inside of the membrane, recording the concentrations of the species in the fluids after passing the inside of the membrane and from these concentrations ascertaining parameters for a correlation between the concentration of the species in the medium to be analyzed on the outside of the membrane and a measurement signal provided by a detector downstream of the membrane.

2. A method according to claim 1, in which the first and second fluids are conveyed along the inside of the membrane at at least one of the same flow rate and in the same throughput volume.

3. A method according to claim 1, in which the concentration of the species one of first and second fluids is zero.

4. A method according to claim 3, in which water is the fluid of concentration zero.

5. A method according to claim 1, in which one of the first and second fluids comprises a carrier liquid used in measuring the concentration of the species in the medium to be analyzed.

6. A method according to claim 1, in which the first fluid and the second fluid are conveyed past the inside of the membrane in immediately successive intervals.

7. A method according to claim 1, in which in a first step the first and second fluids are conveyed simultaneously and parallel to one another on different flow paths past the inside of the membrane, and in a second step the first and second fluids are conveyed simultaneously and parallel to one another past the inside of the membrane with the flow paths interchanged.

8. A method according to claim 1, in which before the first and second fluids are conveyed past the inside of the membrane, a detector arranged behind the membrane is calibrated in a direction of flow of the first and second fluids.

9. A method according to claim 8, in which the method of calibrating the analysis system having a membrane is repeated at at least one of predetermined intervals and in dependence on predetermined external conditions.

10. A method according to claim 8, in which the temperature of the membrane is measured during calibration of the analysis system.

11. An analysis system having a membrane with an outside in contact with a medium to be analyzed and an inside, a flow path on the inside of the membrane which on an input side is connected to a reservoir for a carrier liquid and on an output side is connected to a detector, the input side of the flow path also being connected to an auxiliary reservoir which is filled with a calibration liquid which, in respect of a species in the medium to be analyzed, has a different concentration from the carrier liquid, and having flow control means which convey calibration liquid or carrier liquid past the inside of the membrane, the inside of the membrane being located between the reservoir and the auxiliary reservoir on one side and the detector on an opposite side.

12. An apparatus according to claim 11, in which the flow control means for the carrier and the calibration liquids comprises a pump having an output which is controllable.

* * * * *